United States Patent
Xie et al.

(10) Patent No.: US 10,613,164 B2
(45) Date of Patent: Apr. 7, 2020

(54) MAGNETIC RESONANCE COIL ARRANGEMENT HAVING A FLEXIBLE LOCAL COIL AND A RIGID LOCAL COIL

(71) Applicant: Siemens Healthcare GmbH, Erlangen (DE)

(72) Inventors: Jingyi Xie, Erlangen (DE); Stephan Zink, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 217 days.

(21) Appl. No.: 15/816,195

(22) Filed: Nov. 17, 2017

(65) Prior Publication Data
US 2018/0136293 A1    May 17, 2018

(30) Foreign Application Priority Data
Nov. 17, 2016 (DE) .................. 10 2016 222 635

(51) Int. Cl.
*G01R 33/34* (2006.01)
*A61B 5/055* (2006.01)
*G01R 33/3415* (2006.01)

(52) U.S. Cl.
CPC ........ *G01R 33/34084* (2013.01); *A61B 5/055* (2013.01); *G01R 33/34007* (2013.01); *G01R 33/3415* (2013.01)

(58) Field of Classification Search
None
See application file for complete search history.

(56) References Cited

U.S. PATENT DOCUMENTS

| | | | |
|---|---|---|---|
| 4,897,604 A | 1/1990 | Carlson et al. | |
| 5,617,027 A * | 4/1997 | Decke | G01R 33/341 |
| | | | 324/318 |
| 5,663,646 A | 9/1997 | Kuth et al. | |
| 6,980,002 B1 | 12/2005 | Petropoulos et al. | |
| 7,282,915 B2 | 10/2007 | Giaquinto et al. | |
| 7,315,167 B2 | 1/2008 | Bottcher | |
| 9,733,322 B2 * | 8/2017 | Hardie | G01R 33/3692 |

(Continued)

FOREIGN PATENT DOCUMENTS

| | | |
|---|---|---|
| CN | 105190342 A | 12/2015 |
| CN | 205193262 U | 4/2016 |

(Continued)

OTHER PUBLICATIONS

English language abtract for WO2010057564A1.
Chinese Office Action dated Sep. 18, 2019, for Application No. 201711144325.7.

*Primary Examiner* — Jermele M Hollington
(74) *Attorney, Agent, or Firm* — Schiff Hardin LLP

(57) ABSTRACT

A magnetic resonance coil arrangement for receiving radio-frequency radiation has at least one flexible local coil initially in a planar shape as well as a rigid local coil in a semi-tubular shape. The flexible local coil has first antenna elements for receiving radio-frequency radiation, as well as at least two first connection elements on different sides of the flexible local coil. The rigid local coil has second for receiving radio-frequency radiation, as well as at least two receiving elements. The first connection elements and the receiving element are designed to connect and thereby bend the flexible local coil to the rigid local coil so as to form a tubular overall local coil.

18 Claims, 6 Drawing Sheets

(56) References Cited

U.S. PATENT DOCUMENTS

| | | |
|---|---|---|
| 2005/0107686 A1 | 5/2005 | Chan et al. |
| 2005/0253582 A1 | 11/2005 | Giaquinto et al. |
| 2007/0103153 A1 | 5/2007 | Bottcher |
| 2012/0256633 A1 | 10/2012 | Biber et al. |
| 2016/0033591 A1 | 2/2016 | Leussler et al. |

FOREIGN PATENT DOCUMENTS

| | | |
|---|---|---|
| DE | 19511 796 C2 | 10/1998 |
| DE | 100 11 522 A1 | 9/2001 |
| DE | 10 2005 020 025 A1 | 12/2005 |
| DE | 10 2005 053 280 A1 | 5/2007 |
| DE | 20 2008 015 239 U1 | 4/2010 |
| JP | H06254069 A | 9/1994 |
| WO | WO-2010/057564 A1 | 5/2010 |

\* cited by examiner

FIG 3
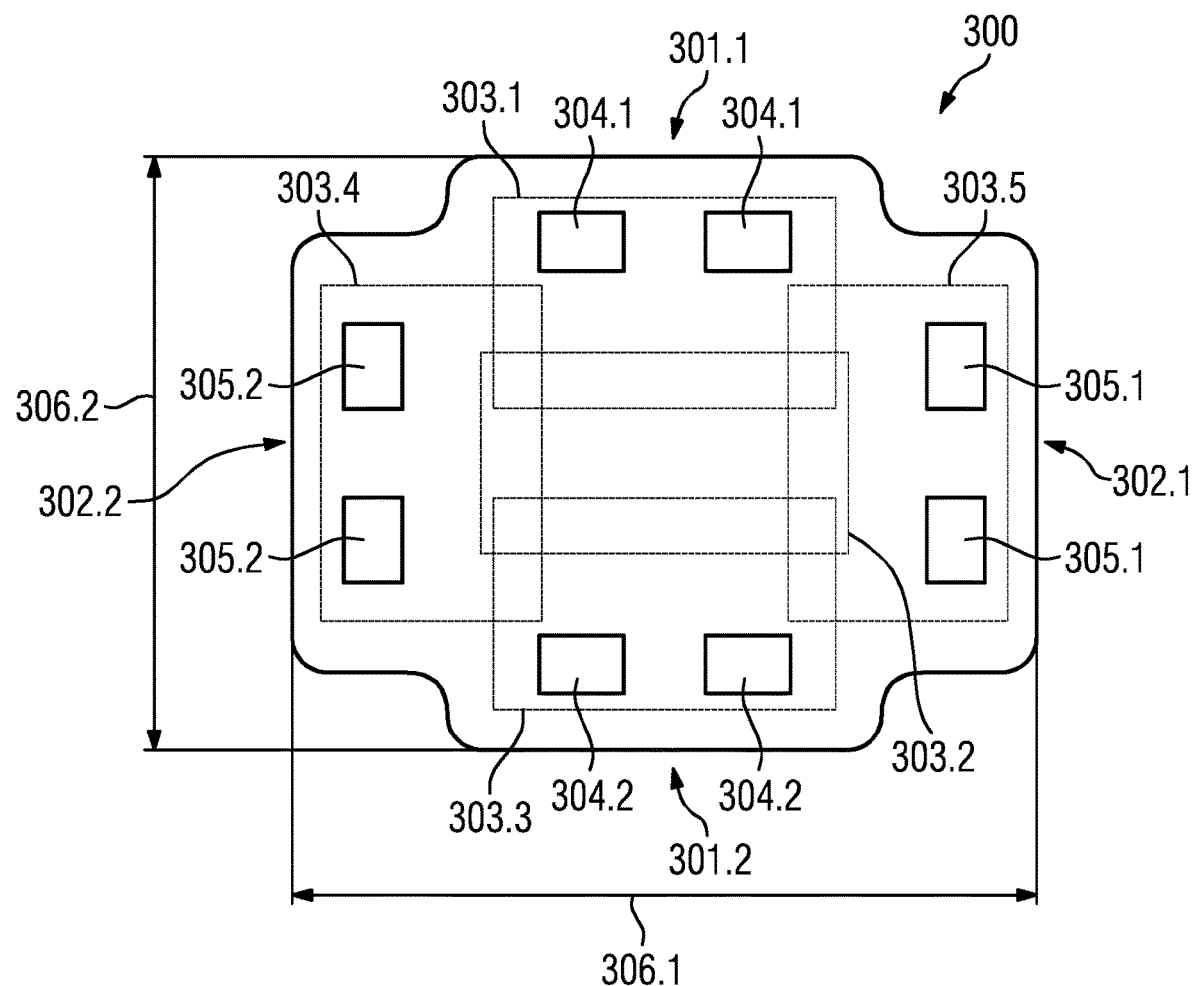
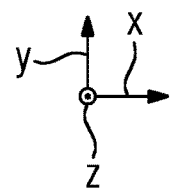

MAGNETIC RESONANCE COIL ARRANGEMENT HAVING A FLEXIBLE LOCAL COIL AND A RIGID LOCAL COIL

BACKGROUND OF THE INVENTION

Related Application

The present application claims the benefit of convention priority under 35 U.S.C. § 119 based on German Application 10201622635.5, filed in the German Patent and Trademark Office on Nov. 17, 2016.

Field of the Invention

The present invention relates to a coil arrangement suitable for use as a local coil arrangement for magnetic resonance imaging.

Description of the Prior Art

Imaging methods are important aids in medical technology. Magnetic resonance (MR imaging), also called magnetic resonance tomography (MRT), is characterized by high and variable soft tissue contrasts. In this modality, excited nuclei, during relaxation thereof, emit radio-frequency electromagnetic magnetic resonance signals that are received by electrically-conductive loops, so-called coils and/or antennas. On receipt, a voltage is induced in the coil by the magnetic resonance signal. These coils are arranged as close as possible to an examination region, in particular to a patient or a part of the patient. It can be advantageous for the coils to surround the examination region at least partly. These coils are therefore also referred to as local coils.

Usually completely rigid local coils are used. These cannot be adapted to the shape and the volume of an examination region however. This means that it cannot be insured that the local coils are arranged as close as possible to the examination region. An inventory of different local coils of various sizes can be maintained in order to select a local coil that is as appropriate as possible for the examination region in question, with a different shape or a different volume. This approach has a high cost, since a number of local coils have to be kept on hand. This process also is inefficient with regard to time, especially if a number of local coils have to be tested on the patient before the suitable local coil is found.

Furthermore, it is known that flexible local coils can be used. These flexible local coils can either be laid on an examination region or can be wrapped around an examination region. A disadvantage of these known flexible local coils is that they easily slide off the intended examination region. Furthermore, when the coil is wrapped around an examination region, overlays of individual antenna elements of the local coil can occur, or the examination region may not be able to be completely surrounded. Both situations are disadvantageous for the signal acquisition and thus for the image quality. Furthermore wrapping the flexible local coil around an examination region represents a very complex working step.

SUMMARY OF THE INVENTION

An object of the present invention is to provide an MR coil arrangement that is able to be adapted rapidly and at low cost to the shape or to the volume of an examination region.

The invention concerns an MR coil arrangement for receiving radio-frequency signals, the coil arrangement having at least one flexible local coil initially in a planar shape as well as a rigid local coil in a semi-tubular shape. The flexible local coil has first antenna elements in planar embodiments for receiving radio-frequency radiation, as well as at least two first connection elements on different sides of the flexible local coil. The rigid local coil has second antenna elements for receiving radio-frequency radiation, as well as at least two receiving elements. The first connection elements and the receiving elements are designed to connect and bend the flexible local coil to the rigid local coil so as to form a local coil that is tubular overall. The coil arrangement is designed to be used in a magnetic resonance tomography apparatus. The different sides of the flexible local coil are opposite sides of the flexible local coil.

The described coil arrangement is able to be adapted to the shape or the volume by the flexibility of the flexible local coil. Furthermore this adaptation is done quickly and a low cost, since the rigid local coil together with the connection elements allows an efficient adjustment of tubular overall local coil. Furthermore it is possible, in various variants of the invention, for various flexible local coils to embody different overall local coils with the same rigid local coil. Since, despite the various overall local coils, the same rigid local coil will always be used, this coil arrangement is less expensive than keeping an inventory of various complete coils for different shapes and volumes of examination regions.

The connection of the flexible local coil to the rigid local coil enables an overall local coil, which surrounds an examination region, to be created rapidly and stably. Here the rigid local coil creates stiffness and resistance to slipping, particularly when the part of the body to be examined is supported on the rigid local coil. This stiffness and resistance to slipping enable the flexible local coil to be connected easily and rapidly to the rigid local coil.

According to a further embodiment of the invention the flexible local coil further has at least two second connection elements. The first connection elements and the receiving elements are designed for the flexible local coil to be used in a first alignment with the rigid local coil so as to form a first tubular overall local coil. Furthermore, the second connection elements and the receiving elements are designed for the flexible local coil to be connected in a second alignment to the rigid local coil so as to form a second tubular overall local coil. The first alignment of the flexible local coil differs from the second alignment of the flexible local coil. In particular, relative to the rigid local coil, the flexible local coil in the first alignment can be orthogonal to the flexible local coil in the second alignment. With the tubular overall local coil formed by the first alignment and the tubular second overall local coil formed by the second alignment, the coil arrangement can be adapted to different shapes and/or volumes of examination regions, when the two alignments differ. Since the coil arrangement is thereby suitable for a number of parts of the body of a patient and/or for a number of patients, a widespread flexibility in use is achieved with this coil arrangement.

In accordance with a further embodiment of the invention, the tubular overall local coil surrounds a first examination volume, and the second tubular overall local coil surrounds a second examination volume. The second examination volume is greater than or equal to the first examination volume. With this embodiment of the invention, the coil arrangement can be adapted especially well to different volumes of examination regions, and thus can be used for imaging of different parts of the body of a patient and/or for different patients. In this way the same coil arrangement can be used both for a child and for an adult, for example. Furthermore, in this way the same coil arrangement can be used for different parts of the human body, such as for the elbow and for the knee. These aspects lead to this coil arrangement being able to be manufactured at lower cost than other coil arrangements with the same usage range.

In a further embodiment of the invention, the flexible local coil has a first number of antenna elements for receiving radio-frequency radiation between the first connection elements, and has a second number of antenna elements for receiving radio-frequency radiation between the second connection elements. Furthermore, in this embodiment of the invention, the second number is greater than or equal to the first number. An antenna element lies between the first connection elements or the second connection elements when it lies at least partly in the rectangle spanned by the first connection elements or the second connection elements. Through this choice of the first and second number, a good quality of the imaging is achieved for different shapes and/or volumes of examination regions, with few artifacts and disturbances. Antenna elements that do not lie between the second connection elements can be designed to be switched off (deactivated). These antenna elements would record only poor-quality image data in many examination situations.

In a further embodiment of the invention, the flexible local coil also has, along the circumference of the first tubular overall local coil between two different sides of the flexible local coil, a first number of first antenna elements for receiving radio-frequency radiation, and has, along the circumference of the second tubular overall local coil between two different sides of the flexible local coil, a second number of second antenna elements for receiving radio-frequency radiation. The second number is greater than the first number. The circumference along a tubular overall local coil in particular includes the part of the flexible local coil that, in the tubular overall local coil, forms a complete tube with the rigid local coil.

In another embodiment of the invention, the flexible local coil extends in a planar manner along a first axis and a second axis, and the flexible local coil in the first alignment is curved along the first axis, and the flexible local coil in the second alignment is curved along the second axis. By such curvature of a planar flexible local coil, a semi-tubular flexible local coil is produced, which is able to be connected especially easily and quickly to the semi-tubular rigid local coil. The curvature around two different axes also makes it possible to enclose different shapes and/or volumes of examination regions.

In a further embodiment of the invention, the first axis is orthogonal to the second axis. Thus an especially large difference is produced between the shape and/or the size of the first examination volume surrounded by the first tubular overall local coil and the shape and/or the size of the second examination volume surrounded by the second tubular overall local coil. This allows significantly different shapes and/or volumes of examination regions to be examined at low cost with just one coil arrangement.

In another embodiment of the invention, the extent of the flexible local coil along the first axis is greater than the extent of the flexible local coil along the second axis. With a flexible local coil embodied in this way, different volumes of examination regions can be examined. This enables various parts of a patient or patients with different body sizes and/or different body weights to be examined at low cost and with just one local coil.

In a further embodiment of the invention, the flexible local coil has a surface aspect ratio of between 1:1 and 1:2, preferably between 9:10 and 1:2, more particularly between 4:5 and 1:2. With such a surface aspect ratio, the difference between the extent along various axes is large enough to encompass different sizes and/or volumes of examination regions for different patients and/or different parts of the body. At the same time, the difference between the extent along various axes is small enough for a further flexible local coil not to be needed for suitable imaging of an examination region, with the size of the volume of this examination region being between the size of the examination volume of the first tubular overall local coil and the size of the volume of the second tubular overall coil. In other words, with such a surface aspect ratio of the flexible local coil, no additional flexible local coil with an intermediate size is needed. This allows the coil arrangement to be used very efficiently, particularly when trials have to be conducted in order to find a size of a local coil that is suitable for a specific examination region.

In another embodiment of the invention, at least one first connection element is arranged, on each side of the flexible local coil, parallel to the first axis. Furthermore at least one second connection element is arranged, on each side of the flexible local coil, parallel to the second axis. The described arrangement of the first connection elements and the second connection elements enables the flexible local coil to be connected especially quickly to the rigid local coil.

In another embodiment of the invention, the flexible local coil is the shape of a planar cross. A first cross bar of the flexible local coil is parallel to the first axis and a second cross bar of the flexible local coil is parallel to the second axis. The first cross bar and the second cross bar have the same width. The first connection elements are embodied as ends of the first cross bar and the second connection elements as sends of the second cross bar. This cross-shaped structure can be manufactured at low cost, since the connection elements are produced by the shape of the flexible local coil and do not have to be connected to the flexible local coil during production as separate parts. At the same time this cross-shaped structure is easy and quick to use, since the connection elements, as part of the structure, are especially robust.

In another embodiment of the invention, the flexible local coil as well as the rigid local coil are designed so as to make a detachable connection. The first connection elements and/or the second connection elements are designed to make a detachable connection with the receiving elements. Such a detachable connection allows a low-cost reuse of the flexible local coil and rigid local coil. Furthermore, with a detachable connection, the overall local coil can particularly tightly surround those examination regions that do not make it possible to remove a tightly-surrounding overall local coil as a whole, such as the ankle joint, the wrist joint or the cervical spine.

In another embodiment of the invention, the flexible local coil as well as the rigid local coil are designed to make a plug connection. The first connection elements and/or the second connection elements can be designed to make a plug connection with the receiving elements. A plug connection enables the flexible local coil and the rigid local coil to be connected especially efficiently and rapidly.

In a further embodiment of the invention, the coil arrangement is designed such that the flexible local coil also has first securing elements and/or the rigid local coil also has second securing elements. The first and/or second securing elements, make a secure connection between the flexible local coil and the rigid local coil. The first securing elements can be integrated into the first connection elements and/or into the second connection elements. The second securing elements can be integrated into the receiving elements. A secure connection prevents an unintentional release of the connection and/or an unintentional displacement of the flexible local coil.

In a further embodiment of the invention, the flexible local coil, as well as the rigid local coil, are each designed to make a secure connection as a click connection, a snap-on connection, a clamping connection, and/or a pin buckle connection. The first securing elements and/or the second securing elements are designed to make such a click connection, a snap-on connection, a clamping connection, and/or a pin buckle connection. These connection types are inexpensive to manufacture and are especially efficient and quick to use for the operator.

In a further embodiment of the invention, the flexible local coil, as well as the rigid local coil, are designed to exchange at least one electric and/or magnetic signal with one another when they form one tubular overall local coil. Through this possible exchange of signals it is not necessary to connect both the flexible local coil and also the rigid local coil to an evaluation unit. Instead, it is sufficient for either the flexible local coil or the rigid local coil to be embodied to be connected to an evaluation unit. The connection can be a cable connection or a wireless connection, for example. This means that the local coil, which is not designed to be connected to the evaluation unit, can be manufactured at lower cost. Furthermore it is faster and more efficient, when using the coil arrangement, to only connect one of the two local coils.

In a further embodiment of the invention, at least one first antenna element of the flexible local coil and at least one second antenna element of the rigid local coil are inductively decoupled by geometrical overlap, when the flexible local coil and the rigid local coil form a tubular overall local coil. This type of decoupling enables crosstalk of antenna elements, in particular crosstalk between the first and the second antenna elements, to be suppressed efficiently and at low cost without further electronic elements.

A local coil is considered herein as rigid if it has a module of elasticity of more than $0.1\ kN/mm^2=0.1\ GPa$, in particular of more than $1\ kN/mm^2=1\ GPa$, in particular of more than $10\ kN/mm^2=10\ GPa$ in relation to a given axis. A local coil is considered herein as flexible if it has a module of elasticity of less than $10\ N/mm^2=10\ MPa$, in particular of less than $1\ N/mm^2=1\ MPa$, in particular of less than $0.1\ N/mm^2=0.1\ MPa$ in relation to a given axis.

A tubular structure can also be curved along its warping direction. A structure is in particular tubular, when more than half, more than 75%, in particular each of the possible two-dimensional cross sections relating to a cross sectional plane orthogonal to the preferred direction, has a convex bore, in particular a circular or an elliptical bore. The outer side of a tubular structure can also be shaped as a prism. A tubular structure can furthermore have cutouts or be formed as a mesh. A tubular structure can thus have function-related or aesthetic openings or cutouts.

A semi-tubular structure can be produced by two cross sections in parallel to the preferred direction through a tubular structure. A structure is i semi-tubular, when more than half, in particular more than 75%, in particular each of the possible two-dimensional cross sections of a cross sectional plane orthogonal to the preferred direction, has an arcuate, elliptical arc shaped or convex arc shaped edge. The structure is semi-tubular if the arcuate edge has an extent of between a quarter circle and a three-quarter circle, between a quarter ellipse and a three-quarter ellipse or between a quarter convex structure and a three-quarter convex structure.

A local coil is considered herein as planar if the extent of the local coil in relation to a first axis and the extent of the local coil in relation to a second axis perpendicular to the first axis is markedly greater, in particular more than twice as great, in particular more than five times as great, in particular more than ten times as great, as its extent in relation to a third axis perpendicular to the first axis and to the second axis.

The examination volume is the three-dimensional space from which magnetic resonance signals are able to be received by means of the tubular overall local coil. The three-dimensional examination volume is considered to be surrounded by the tubular overall local coil, even if it is only surrounded along one circumference around the preferred direction of the tubular overall local coil, i.e. is not enclosed at the two ends of the tubular overall local coil.

The three-dimensional structure, which is to be examined by imaging by means of the tubular overall local coil and an MR device, is considered herein as the examination region. The examination region can be a part of a human body or a phantom. During the examination using a tubular overall local coil, the examination region is part of the examination volume.

An antenna element includes an electric conductor, which preferably is a material with a high electric conductivity, such as copper. An antenna element can also be a singly or multiply wound closed or open conductor loop, and can be formed as a conductor coil. An antenna element receives radio-frequency radiation in an MR device. An antenna element can be coupled to another antenna element by inductive coupling, but also by electric coupling.

A first antenna element and a second antenna element are decoupled by geometrical overlap such that the overlap area resulting from the overlap of the antenna elements is dimensioned so that the magnetic flux passing through the overlap area just cancels out the magnetic flux created in the other areas by the other antenna element.

Radio-frequency radiation is electromagnetic radiation with a frequency of more than 1 MHz, in particular more than 10 MHz, in particular more than 100 MHz.

For a flexible local coil, which extends in a planar manner along a first axis and a second axis, the first main axis of the flexible local coil is the axis (not necessarily identical with the first or the second axis), along which the flexible local coil has its maximum extent. The second main axis is parallel to the plane spanned by the first axis and the second axis and orthogonal to the first main axis. The surface aspect ratio of the flexible local coil is the ratio of the extent n along the second main axis to the extent m along the first main axis. The surface aspect ratio is then often specified as n:m or as 1:(m/n).

BRIEF DESCRIPTION OF THE DRAWINGS

FIG. 3 shows a view from above of a flexible local coil in accordance with the invention.

DESCRIPTION OF THE PREFERRED EMBODIMENTS

Figure 1:
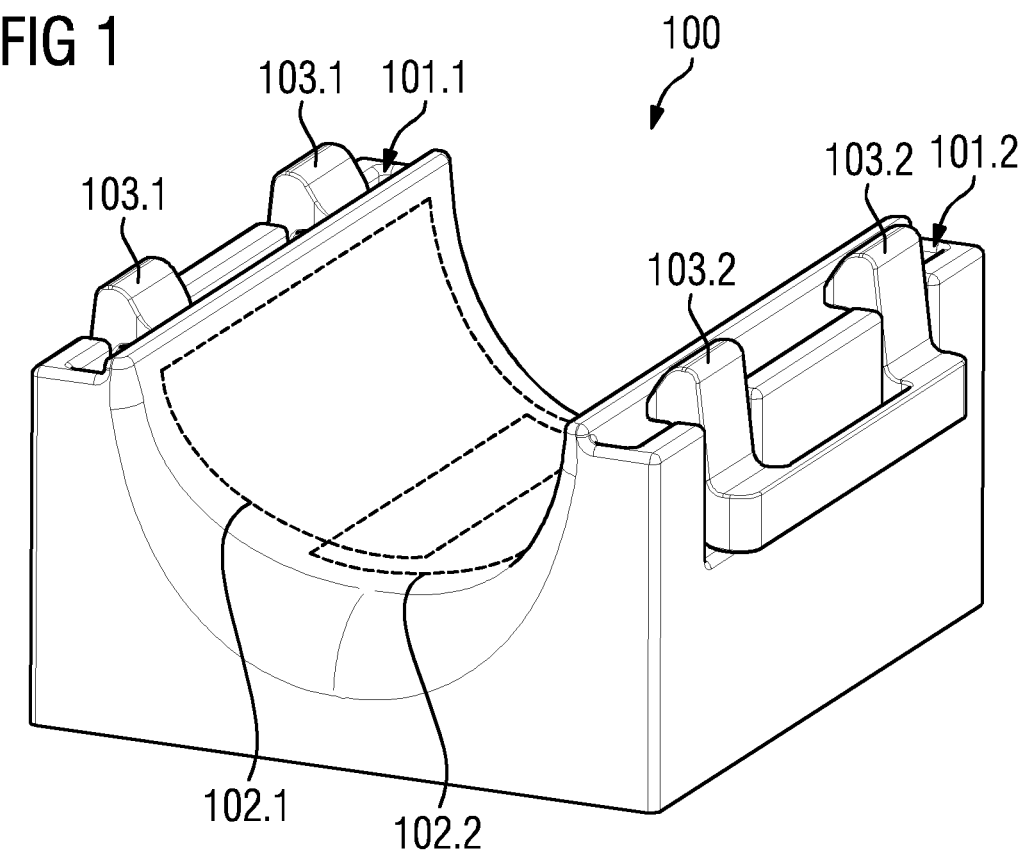
FIG. 1 shows a perspective view of a rigid local coil in accordance with the invention.
Figure 2:
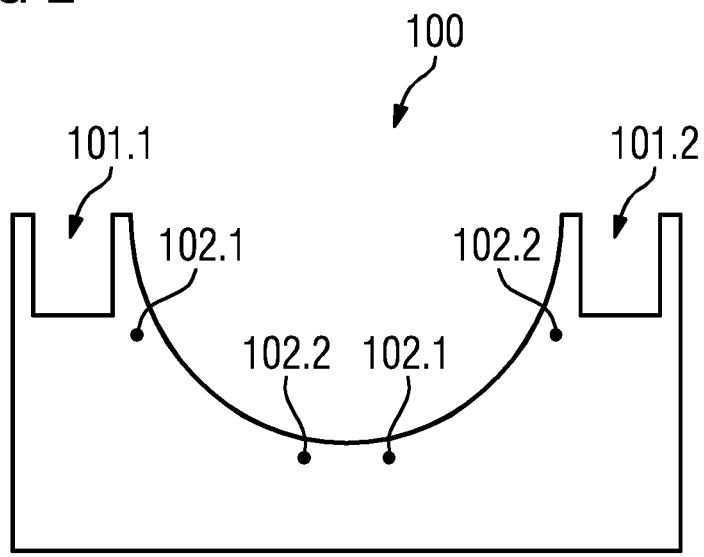
FIG. 2 shows a cross section through a rigid local coil in accordance with the invention.

FIG. 1 shows an exemplary embodiment of a semi-tubular rigid local coil 100, FIG. 2 shows a cross section through the rigid local coil 100. The shape of the rigid local coil 100 essentially corresponds on its outer side to a cube and on its inner side to a tube. The rigid local coil 100 has receiving elements 101.1, 101.2. In the exemplary embodiment shown, the receiving elements 101.1, 101.2 are designed as cutouts in the body of the rigid local coil 100. The receiving elements 101.1, 101.2 are designed to be connected to first connection elements 301.1, 301.2 or second connection elements 302.1, 302.2 of a flexible local coil 300. In the exemplary embodiment shown, the connection is established by plugging the first connection elements 301.1, 301.2 or the second connection elements 302.1, 302.2 into the receiving elements 101.1, 101.2.

The rigid local coil 100 also has second antenna elements 102.1, 102.2. The rigid local coil can have further second antenna elements, which are not shown in FIG. 1 and FIG. 2 for reasons of clarity. The second antenna elements 102.1, 102.2 are, in this exemplary embodiment a singly-wound conductor loops. They can also be embodied as multiply-wound conductor loops. The second antenna elements 102.1, 102.2 receive radio-frequency radiation. The second antenna elements 102.1, 102.2, in the exemplary embodiment shown, are decoupled by geometrical overlap. In the exemplary embodiment shown, at least one second antenna element 102.1, 102.2 is connected to the radio-frequency antenna controller 911, this connection and the radio-frequency antenna controller 911 are not shown in FIG. 1 and FIG. 2. As an alternative at least one second antenna element 102.1, 102.2 can be connected indirectly via the flexible local coil 300 to the radio-frequency antenna controller 911. The rigid local coil 100 can also have electronic elements for reading out signals of the antenna elements 102.1, 102.2 or for processing said signals, these electronic elements are not shown.

In the exemplary embodiment shown, the rigid local coil 100 also has second securing elements 103.1, 103.2. The second securing elements 103.1, 103.2 are designed to make a secure connection to the first securing elements 304.1, 304.2, 305.1, 305.2 of a flexible local coil 300. The second securing elements 103.1, 103.2, in the exemplary embodiment shown, are designed to make a click connection with the first securing elements 304.1, 304.2, 305.1, 305.2. The second securing elements 103.1, 103.2 are designed in this case as lugs, and the first securing elements 304.1, 304.2, 305.1, 305.2 are designed in this case as cutouts, such that the lugs engage in the cutouts and in this way fix the first connection elements 301.1, 301.2 of the flexible local coil 300 into the receiving elements 101.1, 101.2 of the rigid local coil. To release the connection the lugs can be moved outwards with a lever mechanism.

As well as the click connection there are other connections that are also possible, for example a snap-on connection, a clamping connection, pin buckle connection or a Velcro connection. With a snap-on connection the second securing elements 103.1, 103.2 can be designed as snap hooks and the first securing elements 304.1, 304.2, 305.1, 305.2 can be designed as the mating piece to the snap hook. With a clamping connection the first securing elements 304.1, 304.2, 305.1, 305.2 can be designed as hooks and the second securing elements 103.1, 103.2 as clamping levers. With a pin buckle connection the first securing elements 304.1, 304.2, 305.1, 305.2 can be embodied as a strap with holes, and the second securing elements 103.1, 103.2 as a matching buckle with pin. Naturally the first securing elements 304.1, 304.2, 305.1, 305.2 and the second securing elements 103.1, 103.2 can be formed as the other part of these connections in each case.

The rigid local coil 100 can be formed of a plastic, in which second antenna elements 102.1, 102.2 are embedded. The plastic can also be washable, by having a surface coating. A washable design is especially advantageous for easy and rapid cleaning.

Figure 4:
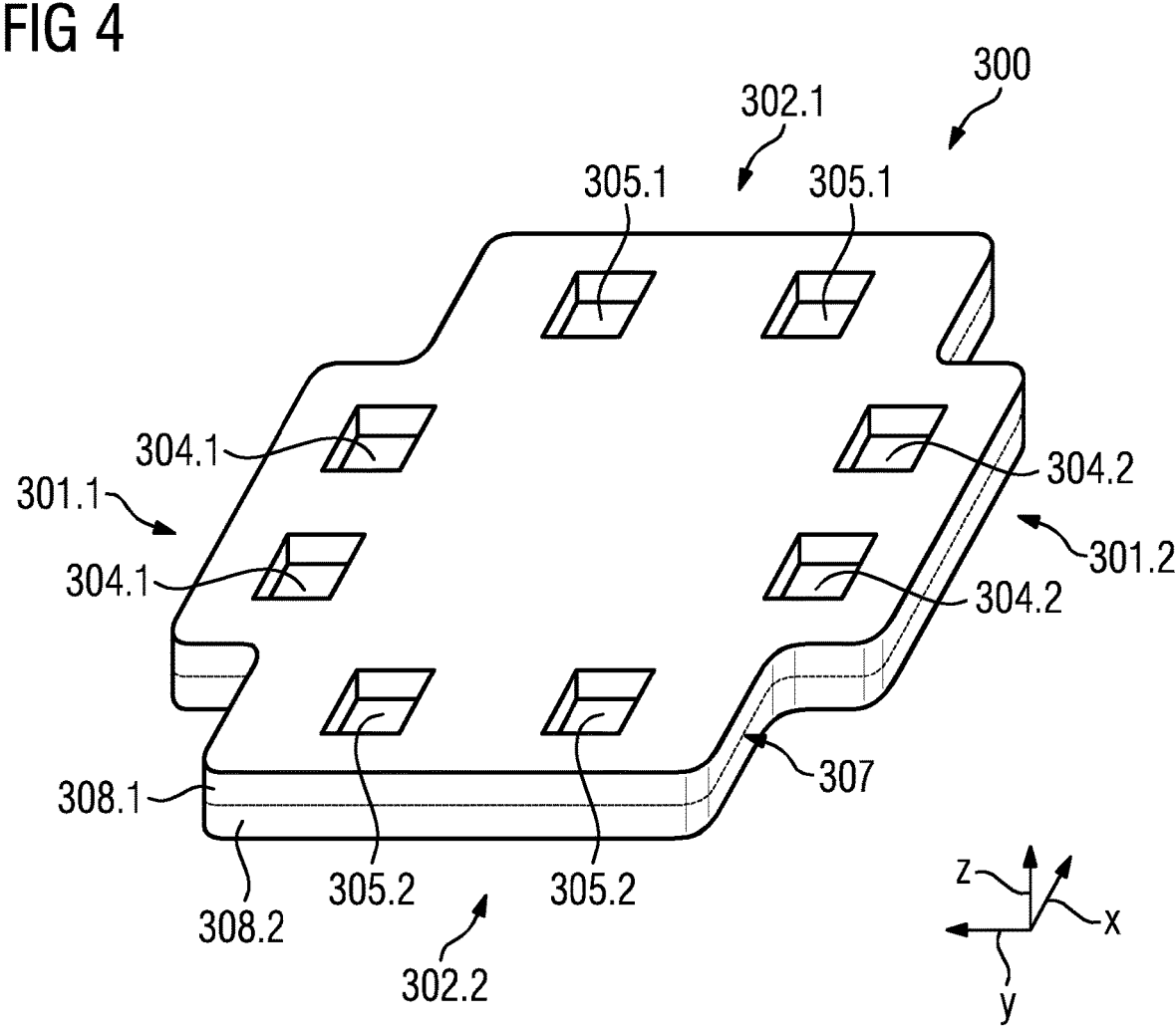
FIG. 4 shows a perspective view of a flexible local coil in accordance with the invention.

FIG. 3 shows a view from above of an exemplary embodiment of a flexible local coil 300 in a planar embodiment, FIG. 4 shows an oblique view of the same exemplary embodiment of a flexible local coil 300 in a planar embodiment. The flexible local coil is in the shape of a planar cross. Other planar geometries are conceivable, however, and planar cross-shaped geometries are also conceivable in which the cross bars are not superimposed in their center. The flexible local coil 300 here has first connection elements 301.1, 301.2 and also second connection elements 302.1, 302.1, which are to be connected by plugging them into the receiving elements 101.1, 101.2 of the rigid local coil 100. The first connection elements 301.1, 301.2 as well as the second connection elements 302.1, 302.1 are, in the exemplary embodiment shown, ends of a cross bar in each case.

The flexible local coil 300 also has first antenna elements 303.1, 303.2, 303.3, 303.4, 303.5. The first antenna elements 303.1, 303.2, 303.3, 303.4, 303.5, in this exemplary embodiment, are singly-wound conductor loops. They can also be formed as multiply-wound conductor loops. The first antenna elements 303.1, 303.2, 303.3, 303.4, 303.5, in the exemplary embodiment shown, can be decoupled by geometrical overlap. For example the antenna element 303.1 can be decoupled from the antenna elements 303.2, 303.4 and 303.5 by geometrical overlap. In the exemplary embodiment shown at least one first antenna element 303.1, 303.2, 303.3, 303.4, 303.5 is connected to the radio-frequency antenna controller 911, this connection and the radio-frequency antenna controller 911 are not shown in FIG. 3 and FIG. 4. As an alternative, at least one first antenna element 303.1, 303.2, 303.3, 303.4, 303.5 can be connected by the rigid local coil 100 to the radio-frequency antenna controller 911. The flexible local coil 300 can also have electronic elements (not shown) for reading out signals of the first antenna elements 303.1, 303.2, 303.3, 303.4, 303.5 or for processing the signals.

The first antenna elements 303.1, 303.2, 303.3, 303.4, 303.5 and the second antenna elements 102.1, 102.2 are designed to receive radio-frequency radiation such that the electromagnetic alternating field of the radio-frequency radiation, in accordance with the Maxwell equations, induces an electric current in at least one part of an antenna element 102.1, 102.2, 303.1, 303.2, 303.3, 303.4, 303.5. This electric current can then be measured.

In the exemplary embodiment shown, the flexible local coil 300 has first securing elements 304.1, 304.2 and also second securing elements 305.1, 305.2. These first securing elements are designed to make a detachable, secured connection with the first securing elements 103.1 and 103.2.

In the exemplary embodiment shown, the flexible local coil 300 is embodied along a first axis X and along a second axis Y in a planar manner. Being designed in a planar manner here means that the extent 306.1 of the flexible local coil 300 in relation to the first axis X, as well as the extent 306.2 of the flexible local coil 300 in relation to the second axis Y, is in each case at least twice as great as the extent of the flexible local coil 300 in relation to a third axis Z, not shown here, wherein the third axis is orthogonal to the first axis X and also orthogonal to the second axis Y. In the exemplary embodiment shown here, the extent 306.1 of the flexible local coil 300 along the first axis X is greater than the extent 306.2 along the second axis Y. Furthermore the depicted exemplary embodiment of a flexible local coil 300 has a planar cross shape. The surface aspect ratio of the flexible local coil is calculated here from the ratio of the extent 306.1 along the first axis X to the extent 306.2 along the second axis Y.

The exemplary embodiment shown has an extent 306.1 of 40 cm along the first axis Y and an extent 306.2 of 30 cm along the second axis Y. This thus produces an approximate surface aspect ratio of 3:4 or 1:1.33. Of course a plurality of other surface aspect ratios can also be realized.

In the exemplary embodiment shown in FIG. 3 and FIG. 4, the flexible local coil 300 has a neutral plane 307 in relation to a curvature about the first axis X and in relation to a curvature about the second axis Y. A neutral plane 307 is said to be that plane of the flexible local coil 300 of which the surface does not change during curvature about the first axis X or about the second axis Y. A neutral plane 307 thus refers to the two-dimensional generalization of a neutral fiber. In the exemplary embodiment shown, the antenna elements 303.1, 303.2, 303.3, 303.4, 303.5 are localized in the neutral plane 307 or close to the neutral plane 307. Close to the neutral plane 307 here means that the distance of an antenna element 303.1, 303.2, 303.3, 303.4, 303.5 from the neutral plane 307 amounts to less than 20% of the maximum thickness of the flexible local coil 300. The maximum thickness of the flexible local coil 300 here designates the maximum extent of the flexible local coil in relation to a third axis Z, which is perpendicular to the surface spanned by the first axis X and the second axis Y.

In the exemplary embodiment shown, the flexible local coil 300 has a first layer 308.1 and a second layer 308.2 of flexible material, which have the same thickness. The flexible material can be foam plastic. The antenna elements 303.1, 303.2, 303.3, 303.4, 303.5 are then arranged between the first layer 308.1 and the second layer 308.2. Such an arrangement makes it possible for any mechanical stresses to be accommodated by the flexible layers 308.1, 308.2 rather than by the antenna elements 303.1, 303.2, 303.3, 303.4, 303.5. Furthermore the flexible local coil 300 can also have other components, for example a flexible protective housing to protect the first and the second layer 308.1, 308.2. The flexible protective housing can consist of a woven material for example.

Figure 5:
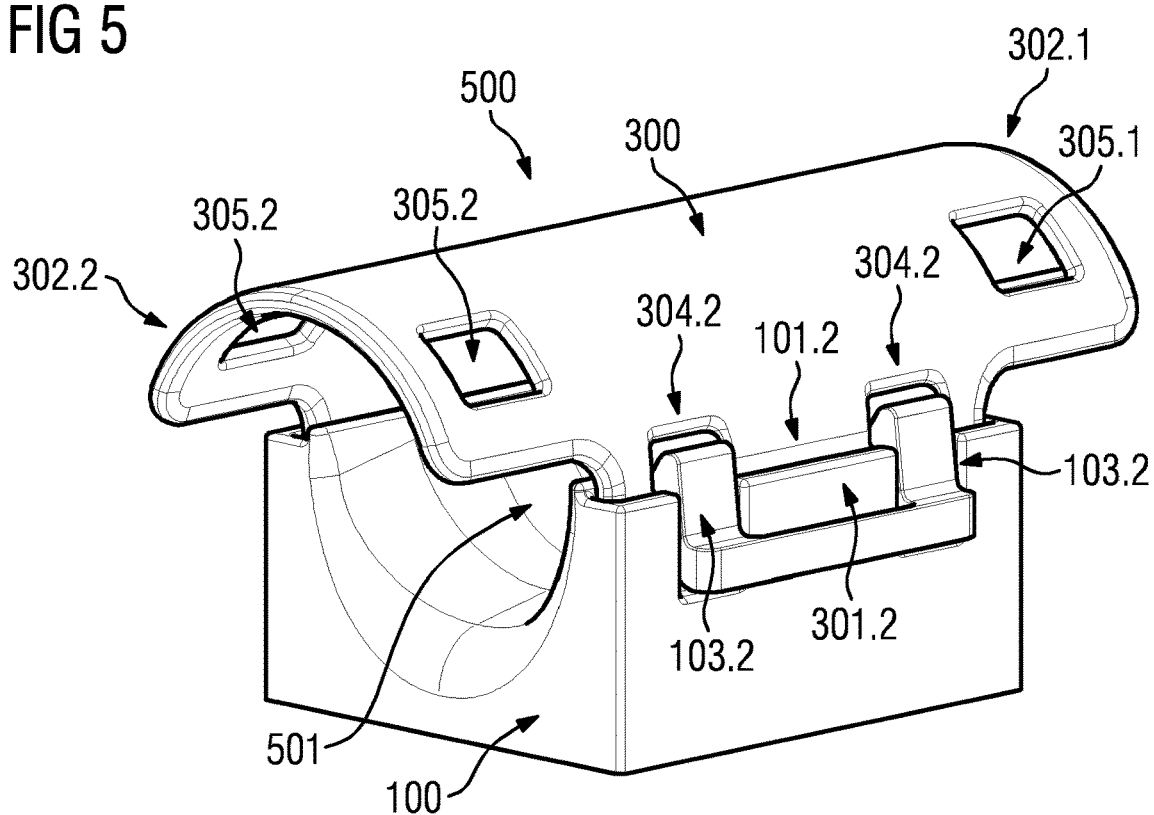
FIG. 5 shows a perspective view of a first tubular overall local coil in accordance with the invention.
Figure 6:
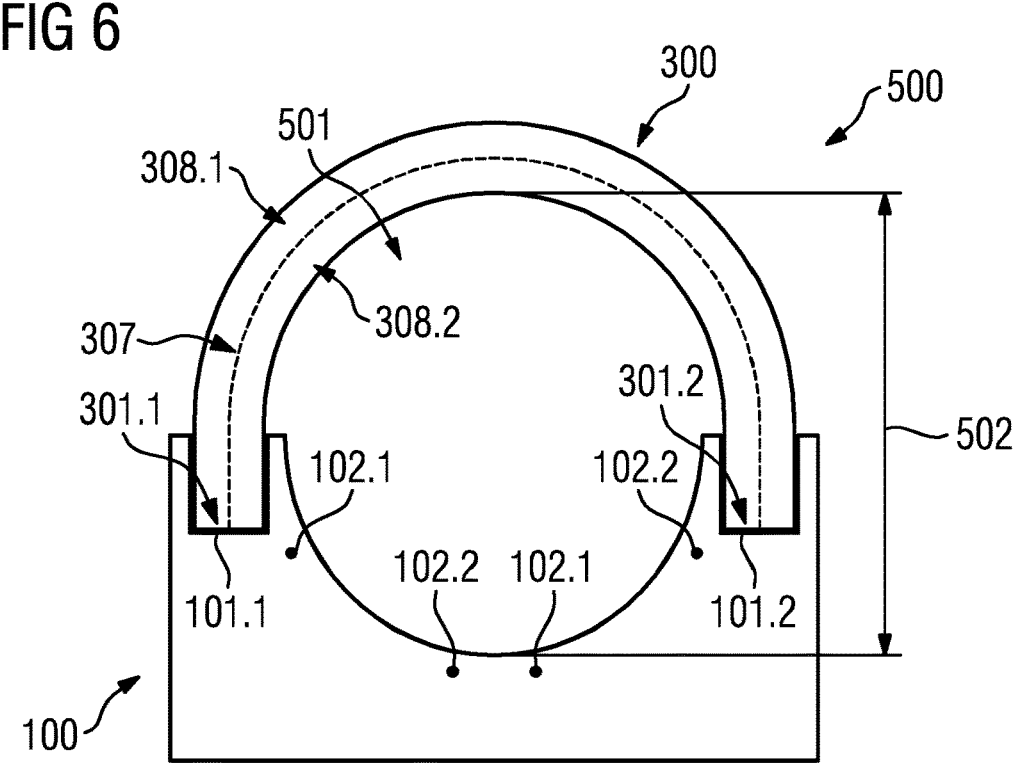
FIG. 6 shows a cross section through a first tubular overall local coil in accordance with the invention.

FIG. 5 shows an exemplary embodiment of a first tubular overall local coil 500, wherein here the flexible local coil 300 is connected in a first alignment to the rigid local coil 100. FIG. 6 shows a cross section through the first tubular overall local coil. For construction of this overall local coil 500 the flexible local coil 300 is curved in relation to the first axis X and is plugged into the rigid local coil 100. Here the first connection elements 301.1 and 301.2 are plugged into the receiving elements 101.1, 101.2, the connection is secured by the first securing elements 304.1, 304.2 and the second securing elements 103.1, 103.2. The tubular overall local coil surrounds an examination volume 501 here. In the configuration shown, the first antenna element 303.3 (not shown in FIG. 5 and FIG. 6) is decoupled from the second antenna element 102.2 of the rigid local coil 100 by geometrical overlap. Furthermore the first antenna element 303.3 (not shown in FIG. 5 and FIG. 6) is decoupled from the second antenna element 102.1 by geometrical overlap. As an alternative other galvanic, capacitive and inductive decoupling techniques are conceivable. In the exemplary embodiment shown, only one first antenna element 303.1, 303.3 is decoupled from a second antenna element 102.1, 102.2 by overlap. As an alternative, one or more first antenna elements can be decoupled in each case from one or more second antenna elements by overlap. In the exemplary embodiment shown, it is possible not to use some of the first antenna elements 303.4, 303.5 (not shown in FIG. 5 and FIG. 6) for the recording of data. In this alignment there are second antenna elements in the rigid local coil for the first antenna elements 303.4, 303.5, which in a plane perpendicular to the preferred direction of the tubular overall local coil together with the first antenna elements 303.4, 303.4 completely surround an examination volume. Therefore the first antenna elements 303.4, 303.5 would not be able to measure a signal comparable in quality to the other first and second antenna elements.

In the exemplary embodiment of FIG. 5 and FIG. 6, a cross section of the first examination volume 501 perpendicular to the preferred axis of the tubular overall local coil 500 has a circumference of 45 cm and thus an average diameter 502 of around 14.3 cm. The diameter in relation to various axes through the cross section can vary because of the flexibility of the flexible local coil. In just the same way other exemplary embodiments are naturally conceivable, in which other circumferences and diameters are produced.

Figure 7:
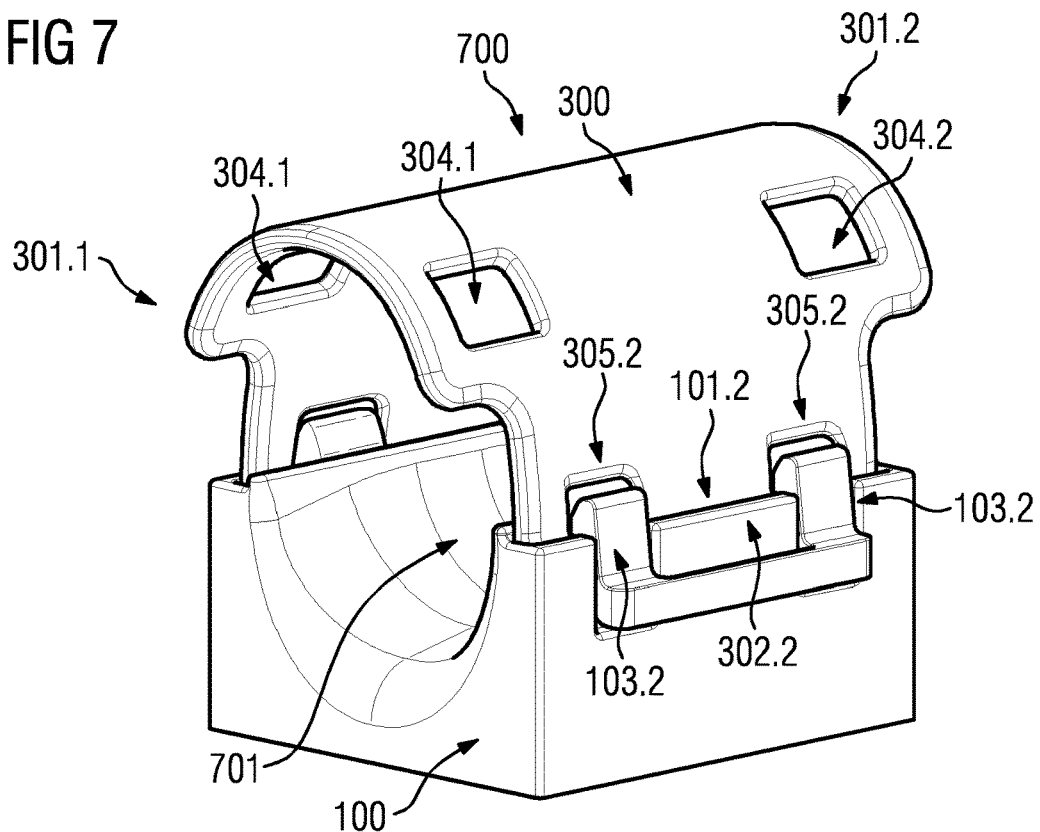
FIG. 7 shows a perspective view of a second tubular overall local coil in accordance with the invention.
Figure 8:
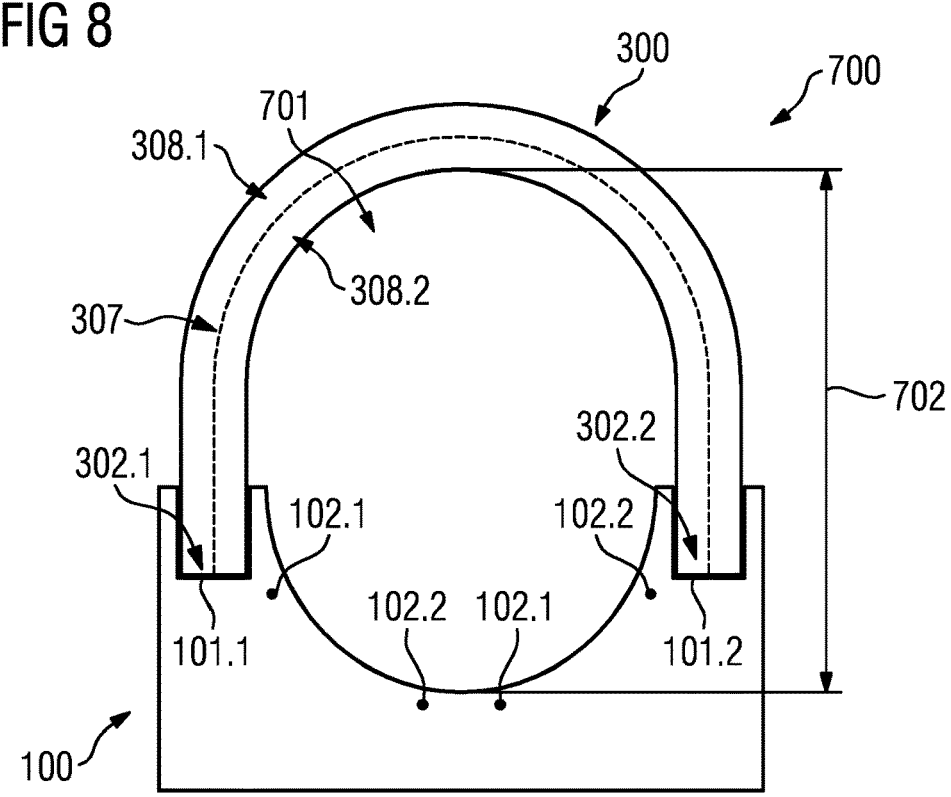
FIG. 8 shows a cross section through a second tubular overall local coil in accordance with the invention.

FIG. 7 shows an exemplary embodiment of a second tubular overall local coil 700, wherein the flexible local coil 300 is connected in a second alignment with the rigid local coil 100, wherein the flexible local coil 300 in the second alignment, by comparison with the flexible local coil 300 in the first alignment, is rotated through 90 degrees. FIG. 8 shows a cross section through the second tubular overall local coil. For construction of the second tubular overall local coil 700, the flexible local coil 300 is bent in relation to the second axis Y and is plugged into the rigid local coil 100. Here the second connection elements 302.1 and 302.2 are plugged into the receiving elements 101.1, 101.2, the connection is secured by the first securing elements 305.1, 305.2 and the second securing elements 103.1, 103.2. The tubular overall local coil surrounds an examination volume 701 here. In the configuration shown, the first antenna element 303.5 (not shown in FIG. 7 and FIG. 8) is decoupled from the second antenna element 102.2 of the rigid local coil 100 by geometrical overlap. Furthermore the first antenna element 303.4 (not shown in FIG. 7 and FIG. 8) is decoupled from the second antenna element 102.1 by geometrical overlap. As an alternative other galvanic, capacitive and inductive decoupling techniques are conceivable. In the exemplary embodiment shown, only one first antenna element 303.4, 303.5 is decoupled in each case from a second antenna element 102.1, 102.2 by overlap. As an alternative, one or more first antenna elements in each case can also be decoupled from one or more of one or more second antenna elements in each case by overlap. In the exemplary embodiment shown, all first antenna elements 303.1, 303.2, 303.3, 303.4, 303.5 of the flexible local coil 300 are able to be used for recording data.

In the exemplary embodiment of FIG. 7 and FIG. 8, a cross section of the first examination volume 701 perpendicular to the preferred axis of the tubular overall local coil 500 has a circumference of 55 cm and thus an average diameter 702 of approximately 17.5 cm. The diameter in relation to various axes through the cross section can vary as a result of the flexibility of the flexible local coil. In just the same way other exemplary embodiments are naturally conceivable, in which other circumferences and diameters are produced.

Figure 9:
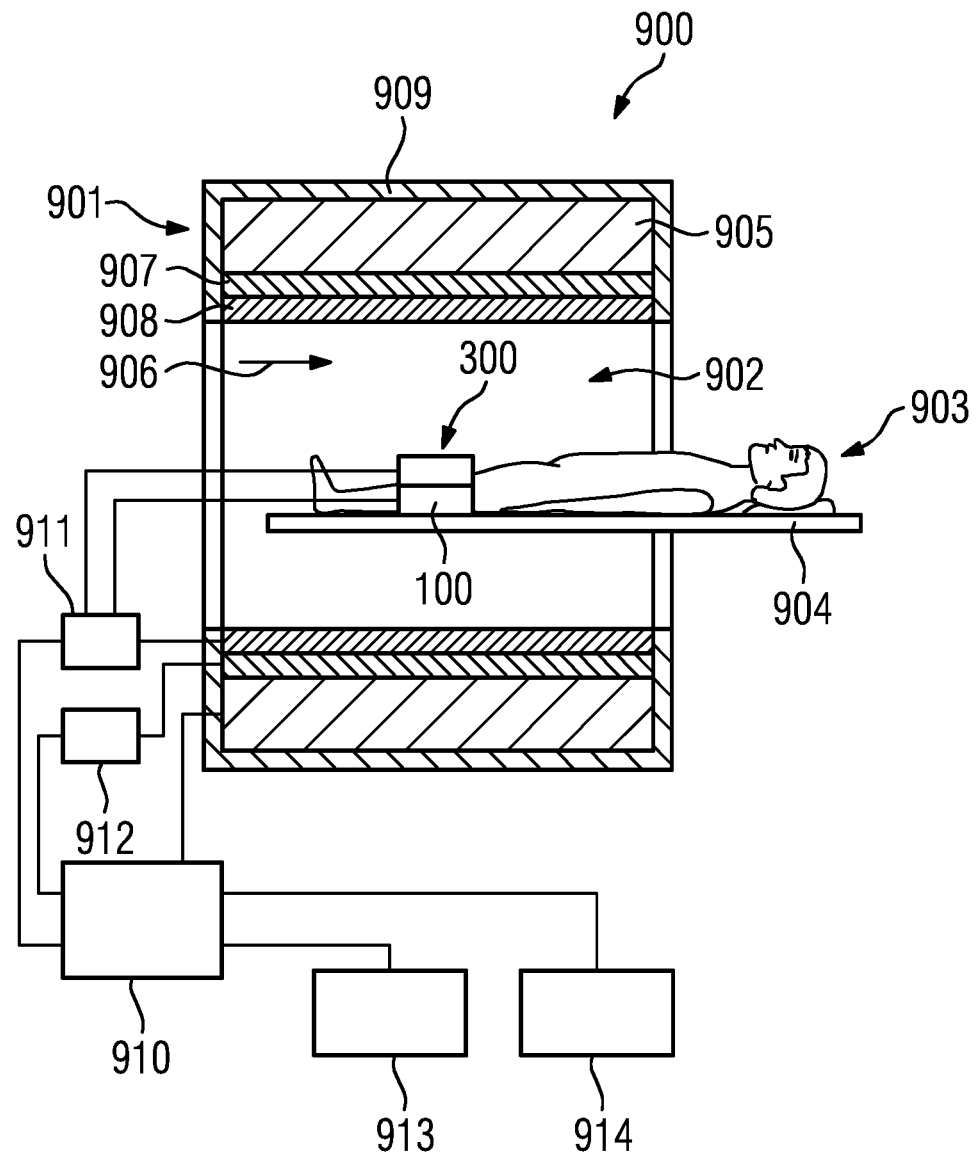
FIG. 9 is a schematic illustration of an MR apparatus with a coil arrangement in accordance with the invention.

FIG. 9 is a block diagram of an MR apparatus 900. The MR apparatus 900 has a data acquisition scanner 901, which has a basic field magnet 905 that produces a strong and temporally constant basic magnetic field 906. The scanner 901 has a patient receiving area 902 for receiving a patient 903. The patient receiving area 902, in the present exemplary embodiment, has a cylindrical shape and is surrounded in a circumferentially by the scanner 901. An embodiment of the patient receiving area 902 differing therefrom is also possible. The patient 903 can be moved by a patient support 904 of the MR apparatus 900 into the patient receiving area 902. To this end, the patient support 904 has a patient table embodied that is movable within the patient receiving area 902. The scanner 901 is screened from the outside by a cladding 909.

The scanner 901 also has a gradient coil arrangement 907 for creating magnetic field gradients, which are used for spatially encoding MR signals during imaging. The gradient coil arrangement 907 is controlled by a gradient controller 912 of the MR apparatus 900. The scanner 901 also has a radio-frequency antenna 908, which in the present exemplary embodiment is a body coil integrated permanently into the scanner 901. The radio-frequency antenna 908 is designed to excite atomic nuclei situated in the basic magnetic field 906. The radio-frequency antenna 908 is controlled by a radio-frequency antenna controller 911 so as to radiate radio-frequency alternating fields into an examination space, which is essentially formed by the patient receiving area 902 of the scanner 901. The radio-frequency antenna 908 is further designed to receive the resulting magnetic resonance signals.

For control of the basic field magnet 905, the gradient controller 907, and the radio-frequency antenna controller 908, the MR apparatus 900 has a system control computer 910. The system control computer 910 centrally controls the MR apparatus 900, such as to carry out a predetermined imaging gradient echo sequence. In addition the system control computer 910 has an evaluation processor for evaluation of medical image data, which are acquired during the magnetic resonance examination. Furthermore the MR apparatus 900 has a user interface, with a display unit 913 and an input unit 914, which are each connected to the system control computer 910. Control information, such as imaging parameters, as well as reconstructed magnetic resonance images, can be displayed on the display unit 913, for example on at least one monitor, for medical operating personnel. Via the input unit 914 information and/or parameters can be entered during a measurement process by the medical operating personnel.

In an MR apparatus 900, radio-frequency pulses are emitted by the radio-frequency antenna 908, so as to cause the nuclear spins of specific atoms to be resonantly excited by these radio-frequency pulses, and flipped by a defined flip angle in relation to the magnetic field lines of the basic magnetic field 906. During the relaxation of the nuclear spins, radio-frequency radiation is emitted, which is received by the antenna elements 102.1, 102.2, 303.1, 303.2, 303.3, 303.4, 303.5 of the local coil 100, 300, and then further processed.

Also a coil arrangement 100, 300, composed of a rigid local coil 100 and a flexible local coil 300, is arranged on the patient support 904, in particular on the patient table. The flexible local coil 300 is connected to the rigid local coil 100. With the use of the coil arrangement 100, 300 radio-frequency signals can be received and transmitted to the radio-frequency antenna controller 911. In the exemplary embodiment shown, both the rigid local coil 100 and the flexible local coil 300 are connected directly to the radio-frequency antenna controller 911. This connection can be made by a cable, or a wireless connection. The rigid local coil 100 and the flexible local coil 300 can exchange signals via contacts or wirelessly, so that only one of the two local coils 100, 300 needs to be connected directly to the radio-frequency antenna controller 911. The coil arrangement 100, 300 is in this case is designed to examine the knee of the patient 903, but it can also be used for other parts of the patient 903, such as the elbow or the head, for example.

A conventional examination of a part of the body using the coil arrangement composed of a rigid local coil 100 and a flexible local coil 300 is carried out with the following steps. First, the rigid local coil 100 is placed on the patient support 904. Furthermore the patient 903 will be placed on the patient support 904, such that the part of the body to be examined lies in the opening of the rigid local coil 100. The flexible local coil 300 is bent along the first axis X or along the second axis Y and is connected to the rigid local coil 100. Subsequently a dataset of raw MR data (k-space data) is recorded by the MR scanner 901. After the recording of this dataset the flexible local coil 300 can be removed from the rigid local coil 100. The acquired dataset is transformed into image data in a known manner, so as to be able to display an MR image of the examination region.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A coil arrangement for receiving radio-frequency radiation, said coil arrangement comprising:
at least one planar flexible local coil;
a rigid local coil having a semi-tubular configuration;
said planar flexible local coil comprising planar first antenna elements configured to receive radio-frequency radiation, at least two first connection elements situated on different sides of said planar flexible local coil, and at least two second connection elements;
said rigid local coil comprising second antenna elements configured to receive radio-frequency radiation, and at least two receiving elements,
wherein the at least two receiving elements are configured to connect at one time to either (i) said at least two first connection elements to connect the planar flexible local coil in a first alignment with the rigid local coil so as to form a first complete tubular-shaped local coil, or (ii) said at least two second connection elements to connect the planar flexible local coil in a second alignment with the rigid local coil so as to form a second complete tubular-shaped local coil, and wherein the first alignment of the planar flexible local coil is different than the second alignment of the planar flexible local coil.

2. A coil arrangement as claimed in claim 1 wherein:
said first complete tubular-shaped local coil surrounds a first examination volume;
said second complete tubular-shaped local coil surrounds a second examination volume; and
said second examination volume is larger than said first examination volume.

3. A coil arrangement as claimed in claim 1, wherein:
said planar flexible local coil has a first number of said first antenna elements between said connection elements, the first number of said first antenna elements configured to receive radio-frequency radiation;
said planar flexible local coil has a second number of said first antenna elements between said second connection elements, the second number of said second antenna elements configured to receive radio-frequency radiation; and
said second number is greater than or equal to said first number.

4. A coil arrangement as claimed in claim 1, wherein:
said planar flexible local coil extends in a plane along a first axis and along a second axis;
said planar flexible local coil, in said first alignment, is curved along said first axis; and
said planar flexible local coil, in said second alignment, is curved along said second axis.

5. A coil arrangement as claimed in claim 4, wherein said first axis is orthogonal to said second axis.

6. A coil arrangement as claimed in claim 4, wherein said planar flexible local coil has an extent along said first axis that is greater than an extent of the planar flexible local coil along said second axis.

7. A coil arrangement as claimed in claim 1, wherein said planar flexible local coil has a surface aspect ratio in a range selected from the group consisting of:
between 1:1 and 1:2,
between 9:10 and 1:2, and
between 4:5 and 1:2.

8. A coil arrangement as claimed in claim 4, wherein:
at least one of the first connection elements, on each side of said planar flexible coil, is situated parallel to said first axis; and
at least one of said second connection elements, on each side of said planar flexible coil, is situated parallel to said second axis.

9. A coil arrangement as claimed in claim 4, wherein:
said planar flexible coil has a planar cross-shaped shape, comprising a first crossbar and a second crossbar;
said first crossbar being parallel to said first axis and said second crossbar being parallel to said second axis;
said first crossbar and said second crossbar have a same width;
said first connection elements are formed as ends of said first crossbar; and
said second connection elements are formed as ends of said second crossbar.

10. A coil arrangement as claimed in claim 1, wherein said planar flexible local coil is detachable from said rigid local coil.

11. A coil arrangement as claimed in claim 10, comprising a plug connection that detachably connects said planar flexible local coil in said rigid local coil.

12. A coil arrangement as claimed in claim 1, wherein at least one of said planar flexible local coil or said rigid local coil comprises securing elements that form a secured connection between said planar flexible local coil and said rigid local coil.

13. A coil arrangement as claimed in claim 12, wherein said securing elements are connectors selected from the group consisting of:
click connectors,
snap-on connectors,
clamping connectors,
pin buckle connectors, and
hook-and-loop connectors.

14. A coil arrangement as claimed in claim 1, wherein said planar flexible local coil and said rigid local coil comprise a coupling configured to exchange at least one of electrical signals and magnetic signals between said planar flexible local coil and said rigid local coil.

15. A coil arrangement as claimed in claim 1, wherein at least one of said first antenna elements and at least one said second antenna elements are inductively decoupled by having a geometrical overlap, when said planar flexible local coil and said rigid local coil form said complete tubular-shaped local coil.

16. The coil arrangement as claimed in claim 1, wherein the first complete tubular-shaped local coil of the at least two first connection elements in the first alignment has a first shape that is different than a second shape associated with the second complete tubular-shaped local coil of the at least two second connection elements in the second alignment.

17. The coil arrangement as claimed in claim 16, wherein the first shape of the first complete tubular-shaped local coil in the first alignment has a first diameter that is different than a second diameter associated with the second shape of the second complete tubular-shaped local coil in the second alignment.

18. The coil arrangement of claim 1, wherein the at least two first connection elements are positioned on the planar flexible local coil perpendicular to the at least two second connection elements.

* * * * *